US008214036B2

(12) United States Patent
   Casset

(10) Patent No.: US 8,214,036 B2
(45) Date of Patent: Jul. 3, 2012

(54) ATRIAL CAPTURE TEST FOR AN ACTIVE IMPLANTABLE MEDICAL DEVICE

(75) Inventor: Cyrille Casset, St Selve (FR)

(73) Assignee: Sorin CRM S.A.S., Clamart (FR)

( * ) Notice: Subject to any disclaimer, the term of this patent is extended or adjusted under 35 U.S.C. 154(b) by 409 days.

(21) Appl. No.: 12/621,326

(22) Filed: Nov. 18, 2009

(65) Prior Publication Data

US 2010/0125309 A1    May 20, 2010

(30) Foreign Application Priority Data

Nov. 19, 2008   (FR) ...................................... 08 06461

(51) Int. Cl.
   *A61N 1/36* (2006.01)
(52) U.S. Cl. ......................................................... 607/9
(58) Field of Classification Search ................ 607/9, 18, 607/19, 27, 28; 600/508, 509
   See application file for complete search history.

(56) References Cited

U.S. PATENT DOCUMENTS

| | | | |
|---|---|---|---|
| 5,304,208 | A | 4/1994 | Inguaggiato et al. |
| 7,203,544 | B2 | 4/2007 | Legay et al. |
| 7,349,737 | B2 | 3/2008 | Amblard |
| 7,483,745 | B2 | 1/2009 | Amblard |
| 2007/0179541 | A1 | 8/2007 | Prakash et al. |
| 2011/0093027 | A1* | 4/2011 | Renesto et al. ................... 607/9 |

FOREIGN PATENT DOCUMENTS

| | | |
|---|---|---|
| EP | 1 407 800 | 4/2004 |
| EP | 1 433 497 | 6/2004 |
| WO | WO 95/19201 | 7/1995 |
| WO | WO 2005/089866 | 9/2005 |

OTHER PUBLICATIONS

Foreign Search Report (Annexe Au Rapport De Recherche Preliminiaire; Ralatif A La Demande De Brevet Francais No. FR 0806461 FA 715104), Jul. 22, 2009.

* cited by examiner

*Primary Examiner* — Brian T Gedeon
(74) *Attorney, Agent, or Firm* — Orrick Herrington & Sutcliffe, LLP

(57) ABSTRACT

An active implantable medical device that is able to perform an atrial capture test. The device includes circuits for delivering atrial stimulation pulses, and testing atrial capture, namely to detect the occurrence of an atrial contraction after the application of an atrial stimulation pulse. An acceleration sensor is used to deliver an EA signal representative of the movements produced by the contractions of the atrial cavity. The EA signal is analyzed to recognize and isolate in this EA signal a component EA4 corresponding to the fourth endocardiac acceleration peak (PEA4) associated with the atrial activity. The presence or absence of this component EA4 is used to define the atrial capture or loss of capture. The signal analysis preferably quantifies an EA parameter (T, T+D), such as the energy of the EA signal within analysis time windows, each having duration D, of successive analysis (W1 . . . Wn) triggered after the atrial stimulation (P) and ending before a ventricular detection or stimulation.

9 Claims, 2 Drawing Sheets

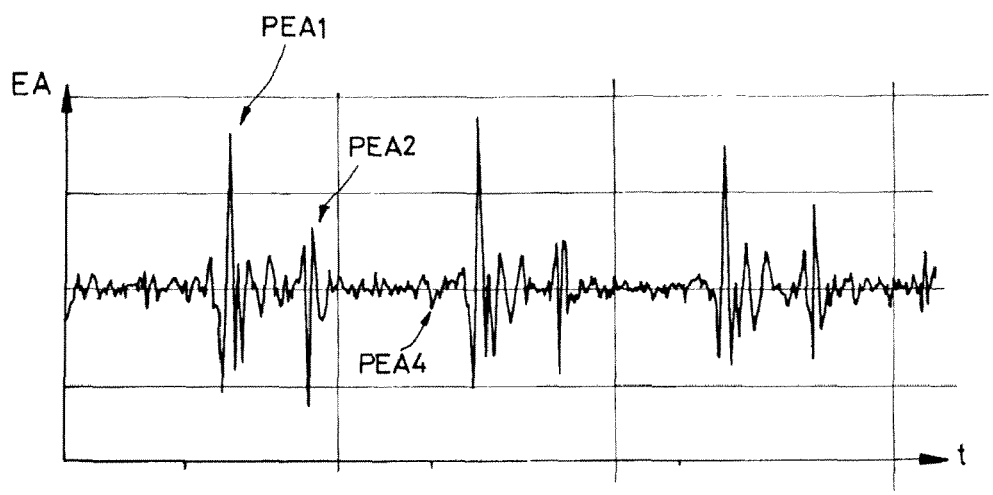
FIG_1
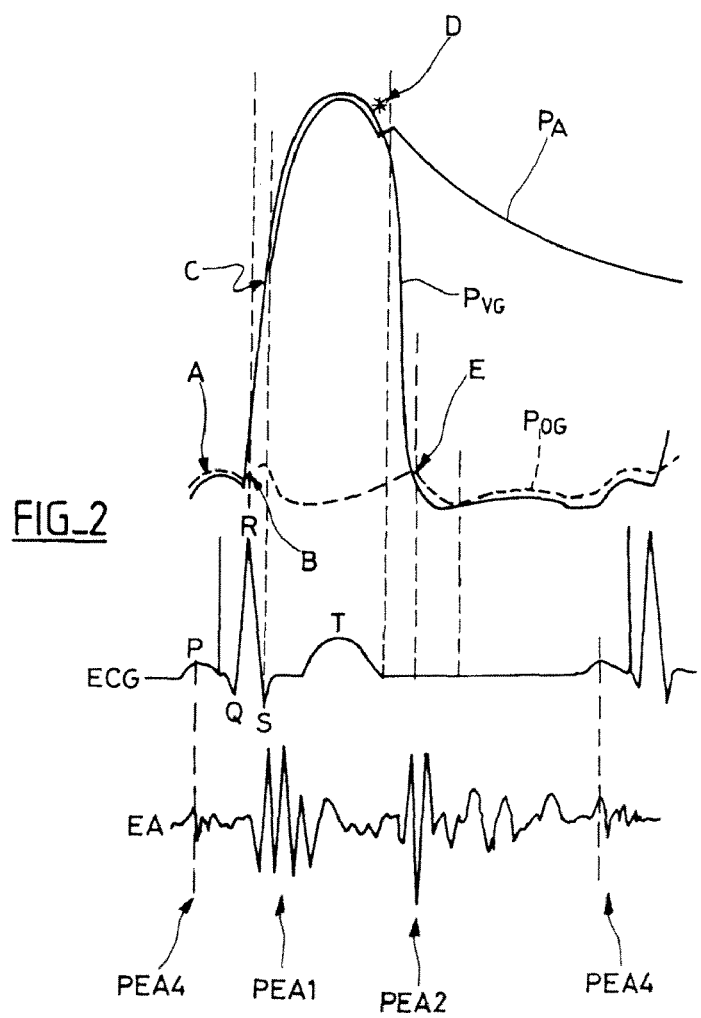
FIG_2

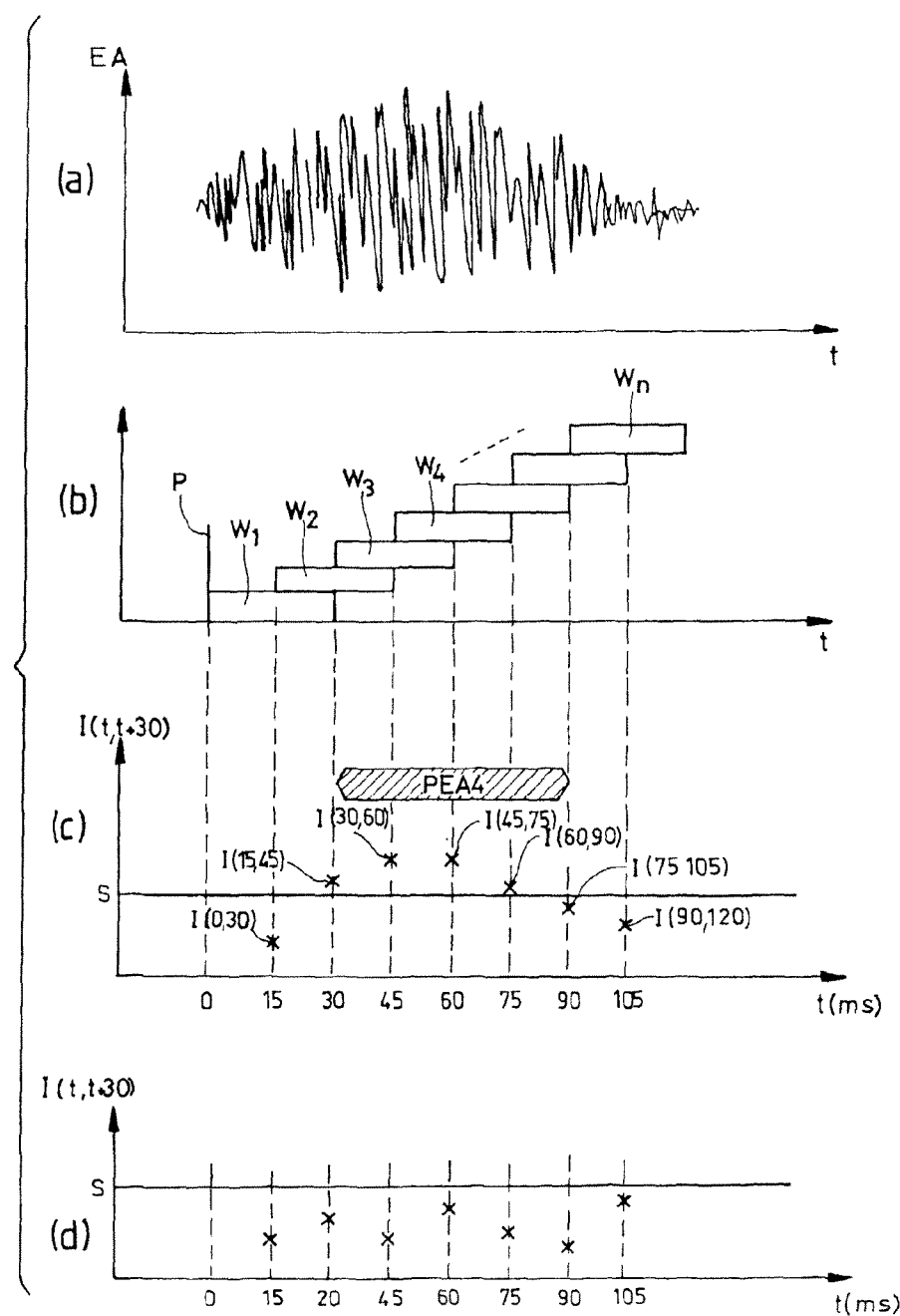

ATRIAL CAPTURE TEST FOR AN ACTIVE IMPLANTABLE MEDICAL DEVICE

CROSS REFERENCE TO RELATED APPLICATIONS

This application claims the priority of French patent application Ser. No. 08/06461, filed on Nov. 19, 2008. The entire disclosures and contents of the above application are hereby incorporated by reference.

FIELD OF THE INVENTION

The present invention relates to "active implantable medical devices" as defined by the Directive 90/385/EEC of 20 Jun. 1990 Council of the European Communities, more particularly to the implantable devices that continuously monitor the cardiac rhythm and deliver electrical pulses to the heart, in response to a detection by the device of a rhythm disorder, as necessary, for stimulation, resynchronization, cardioversion and/or defibrillation. The present invention relates even more particularly to those implantable devices that have at least one detection/stimulation lead for the atrium or both atria, e.g.; pacemaker or defibrillator devices of the following types: atrial single chamber; atrioventricular dual chamber; or "Multisite" triple or quadruple chamber.

BACKGROUND OF THE INVENTION

After delivering a pacing stimulation pulse to the atrium, it is important to detect the "evoked wave", i.e., the depolarization wave induced by pacing the atrium to determine whether the stimulation pulse delivered was effective. This test (known as a "capture test") is used to adjust the pacing stimulation pulse amplitude and/or pulse width. However, in the case of an atrial stimulation, the search for the evoked wave is particularly difficult. Indeed, not only is the amplitude of the evoked wave in the atrium much lower value than the amplitude of the evoked wave in the ventricle, but it also appears much earlier relative to the delivery of the stimulation pulse: the atrial evoked wave (P wave) starts approximately 10 ms after stimulation of the atrium and finishes at about 30 ms—whereas the evoked ventricular wave (R wave) is observed to start at about 60 ms after stimulation.

The very early atrial evoked wave is particularly mixed or even masked in the detection amplifier output of the transient electrical signal called "amplifier response," which follows the electrical stimulation. This "amplifier response" is always present, whether the evoked wave is present or not. More specifically, to discharge the charges appearing at the heart/electrode interface after a stimulation, it is planned to release the stored energy by simultaneously disconnecting or "blanking" the detection circuits of the amplifier, typically for a duration of about 14 ms. Moreover, when the amplifier is reconnected to the poles of the electrode at the end of the blanking period, a transient rebound voltage occurs at the output of the amplifier, and persists a few milliseconds until the amplifier is completely desaturated.

It shall be understood that in these circumstances, it is very difficult to detect the presence of an evoked P wave, for example, as part of an atrial capture test.

EP 1 433 497 A1 and its counterpart U.S. Pat. No. 7,203,544 (ELA Medical) describe a technique to improve the response of the amplifier for atrial detection by a controlled inhibition of atrial detection circuits in order to search for post-stimulation spontaneous complexes after "micro-blanking", the real "blanking" being activated later to allow the complete discharge of stored energy at the heart/electrode interface after the stimulation.

This technique of direct electrical measurement of evoked potentials produced by the atrium requires very precise control over the detection amplifier. It provides a definite improvement, but still does not guarantee safe detection of spontaneous complexes in all clinically feasible circumstances, given the variability of amplitudes, the instants of occurrence, etc., of the electrical potentials that are to be measured to detect the presence or absence of the evoked wave.

EP 1 407 800 A1 and its counterparts U.S. Pat. No. 7,349,737 and U.S. Pat. No. 7,483,745 (ELA Medical) describe another indirect way to detect the evoked atrial wave, by analysis of the intrinsic sinus rhythm of the patient and/or AV conduction delays of the patient's heart. Such indirect methods are, however, limited in their applicability and may particularly be in default in case of atypical cardiac events. For example, one method concerns pacing the atrium and assessing the presence of the conduction to ventricle via a second lead placed in the ventricle of the patient. But this method cannot be implemented in patients with complete atrioventricular block (which is, to be sure, a common problem justifying the initial implantation of a pacemaker). In general, the test function can be tricked by the occurrence of paroxysmal atrioventricular blocks in a patient who does not have the symptoms of a complete block.

The WO 2005/089866 A1 proposes a third approach, different from a direct electrical measurement of the depolarization potential on the atrium, and an indirect determination from the rhythm analysis and from the atrial and ventricular sequencing, which concerns measuring a mechanical characteristic, by detecting the atrial contraction from a signal representing the endocardiac acceleration delivered by an appropriate accelerometer sensor. Such a sensor may be present on the atrial lead or on another lead with a sensor, said lead being placed directly in the atrium or in another position to detect the signal of endocardiac acceleration (EA) signal representative of the contractions of the atrium.

In this third approach, the device, after atrial pacing, uses a functional signal—the EA signal—representative of the cardiac mechanics, instead of a signal originated from the electrical propagation of the depolarization wave. This mechanical signal can also be exploited as a complement of the electrical signal, as described in the US2007/0179541 A1 whose purpose is to measure and analyze the delay between the electrical detection and the mechanical detection of the atrial contraction.

WO2005/089866 A1 suggests to use the EA signal for various purposes such as optimization of the AV delay in the case of a dual chamber stimulation, optimization of the VV delay in the case of the biventricular stimulation for a therapy of Cardiac Resynchronization Therapy (CRT"), detection of the capture in a cardiac cavity, etc.

However, as for the electrical signal, the component of the EA signal corresponding to the atrial activity not only presents a much lower amplitude than in the case of the ventricle, but it also occurs much earlier, which renders its detection and analysis much more difficult. This is believed to be the reason why no technique based on the analysis of the atrial component of the EA signal procuring really exploitable results was proposed until now by the inventors, despite the interest of disposing of a signal directly reflecting the mechanical activity of the heart.

OBJECT AND SUMMARY OF THE INVENTION

It is, therefore, an object of the present invention to overcome the difficulties of detecting the evoked atrial wave, by detecting the evoked atrial wave from the EA signal that reflects both the very early nature and low amplitude of the latter.

The present invention is thus directed to the detection of atrial evoked wave, based upon a measurement of a mechanical characteristic of cardiac activity, by detecting the contraction of the atrium by an endocardiac acceleration signal delivered by an appropriate accelerometer sensor. In one preferred embodiment, the present invention essentially proposes, after having paced the atrium, to use a functional signal (the EA signal) representative of the mechanical heart activity rather than a signal from the electrical propagation of the depolarization wave.

Advantageously, the present invention can be used to detect situations of loss of atrial capture based upon the absence of a contraction of the atrium after an atrial stimulation. The detection of a loss of atrial capture is indeed important because it is necessary in such cases to take immediate and appropriate actions, and/or to modify the functioning of pacemakers, including, for example:

application of an atrial back-up stimulation with a higher energy pulse; and increase the energy of the following atrial pacing pulses.

In the particular case of implantable devices equipped with an automatic switching mode, the detection of a loss of atrial capture can be used to produce a modification of the criteria for a possible switch to a ODD mode for as long as the atrial capture is not restored.

As explained above, the present invention is based on the approach in which detecting the atrial contraction occurs by an analysis of the endocardiac acceleration. Various clinical studies have been conducted which show that the endocardiac acceleration is a parameter that provides comprehensive information about the mechanical heart action, in the case of normal as well as abnormal or deficient operation. The endocardiac acceleration, which is measured by an accelerometer coupled to the heart muscle, indeed reflects very precisely and in real time phenomena related to movements of the heart chamber (the atrial cavity in the case of the present invention).

Thus, EP 0 515 319 A1 and its counterpart U.S. Pat. No. 5,304,208 (Sorin Biomedical Cardio SpA) teach how to collect an EA signal using an endocardial lead incorporating a micro-accelerometer to measure the endocardiac acceleration ("EA").

It should be noted that, although the present invention is discussed in the context of an analysis of an EA signal delivered by an implanted sensor (typically, a sensor placed on an endocardial lead,) the invention is also applicable to an analysis made from an external EA signal collected by suitable non-invasive sensor. Such external EA signal may be, for example, a signal from a sensor fixed on the patient's chest at the sternum.

Here and subsequently, the term "EA signal" or "signal EA", should be understood to cover both an external EA signal, collected by a non-invasive sensor or an endocardial EA signal collected by an acceleration sensor mounted on a cavity introduced into a patient's heart, or an EA signal issued by an epicardium lead located in direct contact with the myocardium.

Broadly, one aspect of the invention is directed to a known implantable device, for example, according to the disclosure of WO2005/089866 A1 cited above, comprising: means for stimulating the atrium, including circuits that are able to deliver pulses of low atrial stimulation energy to be applied to an electrode implanted in the atrial cavity of a patient, and means for testing an atrial capture, able to detect the occurrence of an atrial contraction after the application of an atrial stimulation pulse, said means including: an acceleration sensor having as an output an EA signal representative of the movements produced by the contractions of the atrial cavity; and means for analyzing the EA signal, able to recognize and isolate in the EA signal delivered by the sensor the so called "EA4" component corresponding to the fourth peak of endocardiac acceleration associated to the atrial activity, and to determine the presence or not of said EA4 component, the presence or not of said EA4 component being respectively representative of an atrial capture or an atrial loss of capture.

In accordance with a preferred embodiment of the present invention, the means for analyzing the EA signal preferably includes means to quantify a parameter of the EA signal inside at least one time window of analysis of a predetermined duration. The window is triggered on or after the moment of application of the atrial pacing pulse, and ending on another specific event. Preferably, the quantified parameter is the energy of the EA signal, integrated over the duration of the analysis time window.

In a more preferred embodiment, the means for analyzing the EA signal also includes means for quantifying a parameter of the EA signal within at least one analysis time window of a fixed length. The window is preferably triggered on or after the moment of application of the atrial stimulation pulse and concluded before a specified event such as a ventricular detection or stimulation. Preferably, the quantified parameter is the energy of the EA signal, integrated over the duration of the analysis time window. More preferably, this parameter is quantified for a plurality of temporally successive windows, including windows that are overlapping in time.

In yet another embodiment, the device further comprises a means for comparing the EA signal parameter quantified within a window to a given threshold. This threshold may be a fixed threshold, a configurable threshold, an adaptive threshold recalculated at regular intervals, or an adaptive threshold recalculated on each cardiac cycle comprising a valid atrial event.

In accordance with a preferred embodiment, the capture test may be applied to a device comprising means for searching for the atrial capture threshold, able to change in an iterative way, the energy of the stimulation pulse delivered by said means of atrial stimulation, and to test each time for the atrial capture or loss of capture.

The acceleration sensor may be a endocardial sensor, an epicardial sensor or an external sensor.

BRIEF DESCRIPTION OF THE DRAWINGS

Further features, advantages and characteristics of the present invention will appear to a person of ordinary skill in the art in view of the following detailed description of a preferred embodiment of the present invention, made with reference to the drawings annexed, in which the same numerical references designate items that are identical or functionally similar from one figure to the next, and in which:

FIG. 1 illustrates an example of endocardiac EA signals collected during three successive cardiac cycles;

FIG. 2 is a series of three timing diagrams illustrating various signals characterizing cardiac activity during a given cycle; and FIG. 3 is a series of four timing diagrams showing how the representative PEA4 component detection is made according to a preferred embodiment of the invention.

DETAILED DESCRIPTION OF THE INVENTION

A preferred embodiment of a device in accordance with the present invention will now be described with reference to the drawings.

As regards its software aspects, the invention can be implemented by suitable programming of the software of a known pacemaker, for example, a cardiac pacemaker or defibrillator/cardioverter, including means for collecting a signal provided by endocardial leads and/or one or more implanted sensors. The invention may be applied to known implantable devices such as the Reply family of products produced and marketed by ELA Medical (also known as Sorin CRM), Montrouge, France.

These are devices with programmable microprocessor controlled circuits and control logic that are operated to receive, form and process electrical signals received by implanted electrodes, and to deliver stimulation pulses having suitable energy levels to these electrodes. It is possible to transmit to these devices by telemetry software instructions that will be stored and executed in suitable memory to implement the functions and algorithms of the present invention as described herein. The adaptation of these devices to implement the functions of the present invention is believed to be within the abilities of a person of ordinary skill in the art, and therefore will not be described in detail.

As illustrated in FIG. 1, which is an example of endocardiac acceleration (EA) signals collected during three successive cardiac cycles, the EA signal presents during a cardiac cycle two main peaks corresponding to the two major noises (these are known as sounds S1 and S2 of phonocardiogram) that it is possible to recognize in each cycle of a healthy heart:

The first endocardiac acceleration peak ("PEA1"), whose variations are closely related to changes in pressure in the ventricle (the peak amplitude PEA1 is more precisely correlated to the dP/dt maximum positive change in pressure in the left ventricle);

The second endocardiac acceleration peak ("PEA2"), which corresponds to the phase of ventricular isovolumetric relaxation and is produced by the sudden deceleration of the blood mass in movement in the aorta.

The EA signal components EA1 and EA2 are those that correspond to the two endocardiac acceleration peaks, respectively PEA1 and PEA2. The EA signal, however, also contains two additional components, of much lower amplitude, called EA3 and EA4, corresponding to S3 and S4 sounds of the phonocardiogram.

The present invention focuses on the detection and use of the EA4 component, which is directly related to the presence of an atrial contraction. Essentially, the inventors have discovered that the atrial component signal EA4 can be used to manage the settings of a pacemaker linked to the atrial activity.

This atrial component presents in particular a peak (herein "PEA4") which, as shown in FIG. 1, is located immediately before the PEA1 peak. For this reason, the PEA4 is sometimes called "PEA0" by cardiologists, because, from an electrical point of view, the atrial contraction precedes the ventricular contraction. However, if we consider the blood flow that is pumped by the heart muscle, the contraction of the atrium (corresponding to the component EA4) completes the filling the ventricle in the end of the diastole corresponding to the (EA2 component) and is therefore, in terms of cardiac haemodynamics, after the latter—hence the designation "PEA4".

FIG. 2 illustrates the various signals characterizing the activity of the heart during a cardiac cycle, with: the profile of intracardiac pressures, a track of a surface electrocardiogram (ECG), and the variations in the endocardiac acceleration signal (EA).

On the profile of intracardiac pressures, the $P_A$ characteristic shows the variations in aortic pressure, the $P_{VG}$ shows the pressure variations of the left ventricle, the $P_{OG}$ shows the pressure variations in the left atrium. Points A to E correspond to different phases: A, contraction of the left atrium; B, closure of the mitral valve, C, opening of the aortic valve, D, closure of the aortic valve, and E, opening of the mitral valve.

The ECG signal includes successively: the P wave corresponding to the depolarization of the atrium, the QRS complex corresponding to ventricular depolarization, and the T wave corresponding to the ventricular repolarization.

The endocardiac acceleration signal EA, meanwhile; can be broken down as follows: EA4 is the component corresponding to the contraction of the atrium (P wave), followed by the EA1 component, which began as a result QRS complex and is caused by a combination of the closure of atrio-ventricular valves, the opening of the semi-lunar valves and the contraction of the left ventricle. The EA2 component that follows accompanies the end of ventricular systole and is generated by the closure of semi-lunar valves. The EA3 component is not shown.

Referring to FIG. 3, a series of timing diagrams presents an advantageous embodiment of one implementation in accordance with the present invention for the detection of the EA4 component, notably enabling (i) to detect the presence or absence of a PEA4, peak and (ii) if a PEA4 peak is detected to determine the moments of the start and end of this peak.

The chronogram of FIG. 3a shows the EA signal in the period immediately after atrial pacing, said atrial pacing event being indicated by the P marker on the chronogram in FIG. 3b. This event P triggers a first time window W1 (FIG. 3b having a start time of T and a finish time of T+D), for example, with a preselected duration, e.g., D=30 ms. Over the duration of this window WI an index I (T, T+D) or more generally "I" is calculated e.g., I (0, 30) representative of the EA signal in the interval T=0 to T+D=30 ms. This index I is, for example, determined from the digitized signal values sampled by calculating the integral of the absolute value of this EA signal over this interval W1. The value of the index I for each window thus represents the average power of the EA signal over the duration of that window. In the preferred embodiment, each window is centered on the timing midpoint of the window, here t=15 ms, and is represented by a point on the chronogram represented in FIG. 3c at the abscissa t=15 ms.

This same determination of Index I is repeated for a new window W2, shifted in time relative to window W1 by a prediction time lag, e.g., 15 ms corresponding to the window duration D divided by two). This second determination, therefore, conducted over the interval T=15 to T+D=45 ms for a window W2, gives a new index I (15,45). The determination is thus repeated again for a series of sliding windows W3, Wn, each window being shifted by the same predetermined time by, e.g., 15 ms, compared to the previous window and generating a series of corresponding indices I3, I4 . . . In. The repetition is continued until one of a ventricular event is detected, the index In fall below a threshold S, or a fixed period, typically one hundred milliseconds, expires.

Based on the evaluation described above, it is considered that there is an atrial contraction in the cardiac cycle in question if the index I (T, T+D) is, for at least one of the analysis time windows Wn, above a predetermined threshold S (FIG. 3c). The definition of the threshold S can be arbitrary or adapted to the patient (preferably configurable by the physician) or even can be the result of an adaptive calculation being updated regularly. As a particular example of an adaptive threshold, one can consider a spontaneous atrial event (non-stimulated depolarization of the atrium) and calculate the indices I(0,30), I(15,45), I(30,60) . . . over a given period. The threshold S is then defined as being equal to 50% of the maximum value of all index values thus calculated. The threshold S may be recalculated at regular intervals, typically once a day, or on each atrial event validated by the device.

If the test is performed and used to prove the presence of an atrial contraction, the device determines the moment of the beginning and of the end of the endocardiac acceleration peak EA4 component (PEA4). This can be obtained, for example, by considering the peak to extend from the first index value exceeding the threshold values until the last index value that is still located above the same threshold S as shown in FIG. 3c. Thus, the presence of a PEA4 peak—hence the existence of a contraction of the atrium in response to atrial stimulation—and the moments of start and end of this PEA4 peak can be determined.

This determination may be applied to an atrial capture test. In this regard, the device applies a predefined atrial stimulation energy, and then tests for the presence of the evoked response of the atrium by searching for a PEA4 peak according to the method described just above. The presence of such a PEA4 peak thus reveals the existence of an atrial contraction in response to the stimulation.

The atrial capture test may advantageously be operated as part of a search for an atrial stimulation threshold. To this end, the implantable device applies to the atrium stimulation pulses of decreasing energy and monitors the EA signal for the presence or absence of a responsive EA4 component (PEA4 peak) the algorithm described above.

If the PEA4 component is actually present (i.e., in the example above, if the index I (T, T+D) is higher than the threshold S in at least one of the sliding windows W1, W2, Wn), the device considers that the atrial stimulation is effective. The energy used for the following atrial stimulation is then typically reduced, typically by one fixed amplitude step, for example, 0.25 V. Once the index I (T, T+D) remains below the threshold S (as shown by the "x" marked at the window Wn mid-points on the absissa in FIG. 3d), then the device considers that the stimulation is ineffective. The atrial stimulation threshold is then set to a value higher than the last value applied. In the latter case, a safety stimulation pulse may be delivered at a preselected amplitude so as to cause, in any case, an atrial contraction.

The atrial stimulation threshold thus determined may be stored in the memory of the device, transmitted to a data collection center, or used by the implant to change the amplitude of the applied stimulation.

For further details on the algorithms for adjusting the amplitude of stimulation from successive capture tests, one can refer in particular to EP 1 080 744 A1 and its counterpart U.S. Pat. No. 6,487,451 (ELA Medical), which describes various techniques for measuring the threshold, of consistency control of the measures for adjusting the width and amplitude of the pulse stimulation. The corresponding algorithms can be implemented using, instead of the detection of an electrical depolarization of the atrium, the capture test conducted in accordance with the teachings of the present invention, i.e., by analysis of the EA signal and search for the presence of an EA4 component.

One skilled in the art will appreciate that the present invention can be practiced by other than the described embodiments, which are presented for purposes of illustration and not of limitation.

The invention claimed is:

1. An active implantable medical device of the cardiac pacemaker, resynchronization, cardioversion and/or defibrillation type, comprising:

means for producing low energy atrial stimulation pulses (P) to be applied to an electrode implanted on the atrial cavity of a patient; and means for detecting an occurrence of an atrial contraction after the application of an atrial stimulation pulse P, said means comprising:

an acceleration sensor having an endocardiac acceleration output (EA) signal representative of movements produced by the contractions of the atrial cavity;

means for analyzing the EA signal to recognize and isolate in the EA signal an EA4 component corresponding to a fourth peak of endocardiac acceleration associated to the atrial activity, including means for determining the presence or absence of said EA4 component, the presence of said EA4 component being representative of an atrial capture and the absence of said EA4 component being representative of an atrial loss of capture; and means for quantifying a parameter of the EA signal within at least one analysis time window, wherein the at least one analysis time window is triggered to begin at or after the moment of application of the atrial stimulation pulse (P), and terminate before a second specific event, and the quantified parameter is representative of energy of the EA signal over the duration of the at least one analysis time window.

2. The device of claim 1 wherein the at least one analysis time window has a fixed duration and the quantified parameter is the energy of the EA signal integrated over said fixed duration.

3. The device of claim 1, wherein the said second specific event is an event selected from among the group consisting of a ventricular detection, a ventricular stimulation, an appearance of an EA1 signal, and a fixed delay period.

4. The device of claim 3, wherein the at least one analysis time window further comprise a plurality of analysis time windows (W1 . . . Wn) successively shifted in time wherein the means for quantifying the EA signal parameter further comprises means for qualifying a parameter I(T, T+D) for at least a first subset of said plurality of successive analysis windows.

5. The device of claim 4, wherein the plurality of successive analysis windows (W1 . . . Wn) are overlapping in time.

6. The device of claim 1, wherein the means for analyzing the EA signal further comprises means for comparing the parameter of the EA signal quantified in the time window (Wi) to a given threshold (S).

7. The device of claim 6, wherein the threshold S is a threshold selected from among the group consisting of a fixed threshold; a parameterizable threshold; an adaptive threshold recalculated at regular intervals; an adaptive threshold that recalculated on each cycle having a valid atrial event.

8. The device of claim 1, further comprising means for searching an atrial capture threshold, including means for changing in an iterative way the low energy of the produced atrial stimulation pulse, and means for testing for an atrial capture or loss of capture in response to said changing low energy atrial stimulation pulses.

9. The device of claim 1, wherein the acceleration sensor is selected from among the group consisting of an endocardial sensor; an epicardial sensor; and an external sensor.

* * * * *